United States Patent [19]

Sheu et al.

[11] Patent Number: 5,514,204

[45] Date of Patent: May 7, 1996

[54] PROCESS FOR THE PURIFICATION OF NITRIC OXIDE

[75] Inventors: Lien-Lung Sheu, Scotch Plains; Ramakrishnan Ramachandran, Allendale; Theodore R. Galica, Glen Gardner, all of N.J.

[73] Assignee: The BOC Group, Inc., New Providence, N.J.

[21] Appl. No.: 271,592

[22] Filed: Jul. 7, 1994

[51] Int. Cl.⁶ .......................... B01D 53/04; B01D 53/14
[52] U.S. Cl. .................... 95/92; 95/121; 95/129; 95/232
[58] Field of Search ............... 95/117, 121, 128, 95/129, 137, 232, 235, 92; 423/239.2, 244.11, 385, 405

[56] References Cited

U.S. PATENT DOCUMENTS

| | | |
|---|---|---|
| 2,568,396 | 9/1951 | James . |
| 2,647,822 | 8/1953 | Pike ........................ 95/129 X |
| 3,489,515 | 1/1970 | Jockers et al. ............. 95/232 X |
| 3,508,382 | 4/1970 | Schoofs et al. ............... 95/129 |
| 3,517,484 | 6/1970 | Lee et al. .................... 95/129 |
| 3,689,212 | 9/1972 | Petit et al. ................ 95/117 X |
| 3,808,327 | 4/1974 | Roberts ..................... 95/129 X |
| 4,149,858 | 4/1979 | Noack et al. .............. 95/129 X |
| 4,153,429 | 5/1979 | Matthews et al. ............ 95/117 |
| 4,156,598 | 5/1979 | Woytek et al. ............ 95/117 X |
| 4,507,271 | 3/1985 | Van Deyck et al. ........ 95/129 X |
| 4,533,365 | 8/1985 | Ringel ..................... 95/129 X |

FOREIGN PATENT DOCUMENTS

| | | | |
|---|---|---|---|
| 1965560 | 7/1970 | Germany | 95/129 |
| 2829703 | 1/1980 | Germany | 95/129 |
| 49-134572 | 12/1974 | Japan | 95/117 |
| 51-028574 | 3/1976 | Japan | 95/129 |
| 55-039233 | 3/1980 | Japan | 95/129 |
| 1357053 | 12/1987 | U.S.S.R. | 95/129 |

*Primary Examiner*—Robert Spitzer
*Attorney, Agent, or Firm*—Coleman R. Reap; Larry R. Cassett

[57] ABSTRACT

A gas mixture comprised of nitric oxide and, optionally an inert gas, and containing small amounts of nitrogen dioxide, and perhaps moisture and sulfur dioxide, is purified by passing the gas stream through a bed of metal cation-free silica, alumina, or zeolite. The concentration of nitrogen dioxide, sulfur dioxide and moisture in the gas stream are significantly reduced as the gas mixture passes through the bed of adsorbent.

25 Claims, No Drawings

5,514,204

PROCESS FOR THE PURIFICATION OF NITRIC OXIDE

FIELD OF THE INVENTION

The present invention is directed to a process for purifying nitric oxide, and more particularly to a process in which nitrogen dioxide is removed from nitric oxide by adsorption.

BACKGROUND OF THE INVENTION

Nitric oxide has recently been found to play an important role in life processes in humans and animals. For example, it helps maintain blood pressure by dilating blood vessels, and kills foreign invaders in the body's immune system. Studies indicate that extraordinary benefits may be obtained by administering small dosages of nitric oxide to patients who suffer from certain illnesses or diseases. Of particular interest is the prospect of reducing pulmonary vasoconstriction in pediatric patients with congenital heart disease complicated by pulmonary artery hypertension by having the patients inhale oxygen-enriched air containing very small concentrations of nitric oxide.

Nitric oxide is a relatively stable gas when it is in the pure state or mixed with an inert gas, such as nitrogen or argon. However when it is mixed with oxygen it reacts rapidly with the oxygen to form nitrogen dioxide, a substance that is highly toxic to humans. The nitrogen dioxide reacts with water to form nitric and nitrous acids, which, when inhaled can cause severe pulmonary oedema, acid pneumonitis or even death. Because of the highly toxic character of nitrogen dioxide, nitric oxide that is intended for inhalation use by humans is generally purified to remove any nitrogen dioxide that is initially in the nitric oxide product as a result of the manufacturing process, and the purified product is stored and shipped in an oxygen-free environment to prevent the subsequent generation of nitrogen dioxide in the storage or shipping container.

Nitric oxide is generally administered to a patient by diluting a nitrogen-nitric oxide concentrate gas containing about 1000 ppm nitric oxide with oxygen or oxygen-enriched air carrier gas to produce an inhalation gas containing nitric oxide in the desired concentration range (usually about 0.5 to 200 ppm, based on the total volume of the inhalation gas). Calculations based on nitric oxide chemical kinetics suggest that if pure oxygen is mixed with the above-described nitrogen-nitric oxide concentrate to produce a gas mixture having a nitric oxide concentration of 200 ppm, it takes only about 3 seconds for the concentration of nitrogen dioxide in the gas mixture to build up to 3 ppm. The currently accepted upper limit for nitrogen dioxide inhalation is 5 ppm (based on the total volume of breathing gas being inhaled). Assuming that this gas mixture is inhaled by a patient within 3 seconds after mixing the nitrogen-nitric oxide concentrate and oxygen, the amount of nitrogen dioxide initially present in the nitric oxide-nitrogen concentrate would have to be very low to ensure that the nitrogen dioxide concentration in the inhalation gas does not exceed 5 ppm. To minimize the risk of exceeding the 5 ppm upper limit, it is desirable that the concentration of nitrogen dioxide in the nitrogen-nitric oxide supply vessel be as low as possible, and it is most preferred that it not exceed about 1 ppm.

Nitrogen dioxide is produced as a byproduct of most, if not all, nitric oxide production processes. Various techniques are employed to remove nitrogen dioxide from the nitric oxide. U.S. Pat. No. 3,489,515 discloses the purification of nitric oxide by washing the nitric oxide with a dilute aqueous solution of nitric acid. The water reacts with the nitrogen dioxide to produce nitric and nitrous acids, which can be washed from the gaseous product stream by washing the stream with water. This method is not satisfactory for producing medical grade nitric oxide because it does not adequately reduce the concentration of nitrogen dioxide in the product gas stream. Nitrogen dioxide can also be removed from nitric oxide by cryogenic distillation. This method likewise leaves a lot to be desired because of the high capital cost of distillation equipment and because not all of the valuable nitric oxide is recovered during the distillation.

Another purification technique that has been reported is adsorption using as adsorbent a bed of the activated coke or activated charcoal (see U.S. Pat. Nos. 2,568,396 and 4,149,858). This procedure suffers from the disadvantages that the activated coke and activated charcoal do not efficiently remove nitrogen dioxide from the gas stream, they adsorb more nitric oxide than is desired and they tend to catalyze the disproportionation of nitric oxide to nitrogen dioxide and nitrogen.

It is known that certain zeolites adsorb nitrogen dioxide from gas streams containing nitric oxide and nitrogen dioxide without also adsorbing the nitric oxide in the gas stream. For example, U.S. Pat. No. 4,153,429, issued to Matthews et al, which relates to the removal of $NO_x$ from gas streams, discloses the use of zeolite Y adsorbent containing 8 to 30 equivalent percent metal cations to remove nitrogen dioxide from a gas mixture. The patentees assert that zeolites do not adsorb nitric oxide, and to eliminate nitric oxide from the gas mixture, stoichiometric quantities of oxygen must be present with respect to the quantity of nitric oxide to be removed from the gas stream. Nitric oxide is oxidized to nitrogen dioxide in the presence of oxygen.

Copending U.S. patent application Ser. No. 129,647, filed Sep. 30, 1993, discloses the removal of nitrogen dioxide from a nitric oxide gas stream by passing the gas stream through a zeolite selected from types A, X and Y zeolites, mordenite, faujasite and chabazite. Although these adsorbents exhibit superior nitrogen dioxide adsorption properties it has been found that they also possess the undesirable attribute of catalyzing the disproportionation of nitric oxide to nitrogen dioxide and nitrogen. It is believed that the metal cations on the zeolite causes the catalytic reaction.

Because of the high toxicity of nitrogen dioxide, highly effective methods for purifying nitric oxide intended for use in medical applications, without concomitantly producing additional nitrogen dioxide, are continuously sought. The present invention provides a simple and efficient method of achieving this objective.

SUMMARY OF THE INVENTION

In one embodiment of the invention, a nitric oxide gas stream containing one or more impurities, including nitrogen dioxide, is purified by passing the gas stream through the bed of metal cation-free silica, alumina or zeolite, thereby removing nitrogen dioxide from the gas stream. The concentration of nitrogen dioxide in the gas stream is generally reduced to not more than about 700 ppm, and is preferably reduced to no more than about 10 ppm, and most preferably reduced to no more than about 3 ppm.

According to a preferred aspect of this embodiment of the invention, the concentration of nitrogen dioxide in the gas stream being treated is reduced to a concentration of about 5000 ppm or less by washing the gas stream with dilute nitric acid and/or water and the washed gas stream is passed through a bed of one or more of the above-mentioned adsorbents to remove nitrogen dioxide. The concentration of nitrogen dioxide exiting the bed of adsorbent is generally reduced to not more than about 700 ppm, and is preferably reduced to no more than about 10 ppm, and is most preferably reduced to no more than about 3 ppm.

In another embodiment, the nitric oxide gas stream is diluted with a sufficient amount of an inert gas, such as nitrogen or argon, to reduce the concentration of nitric oxide in the gas stream to a predetermined concentration, generally to about 5 to about 5000 ppm, and the diluted gas mixture is further purified by passing it through the bed of metal cation-free silica, alumina or zeolite, thereby reducing the concentration of nitrogen dioxide in the diluted gas stream to the desired level.

In a third embodiment, the nitric oxide gas stream is first partially purified by passing it through the bed of metal cation-free silica, alumina or zeolite, thereby reducing the concentration of nitrogen dioxide in the gas stream to a given level, and the partially purified gas stream is diluted with a sufficient amount of an inert gas, such as nitrogen, argon or helium, to reduce the concentration of nitric oxide in the gas stream to the desired final concentration, generally to about 5 to about 5000 ppm.

The conditions under which the adsorption is carried out are not critical. It can be carried out at temperatures in the range of about −50° to about 300° C. or higher, and at absolute pressures in the range of about 0.5 to about 200 bar or higher. To simplify the process, the adsorption is preferably carried out at temperatures in the range of about 0° to about 100° C. and at absolute pressures in the range of 1 to about 10 bar.

The adsorption can be carried out in a single bed of adsorbent or in a battery of two or more adsorption beds arranged in parallel and operated out of phase, so that at least one bed is undergoing adsorption while the adsorbent in another bed is being replaced or regenerated.

In one embodiment of the invention, a nitric oxide gas stream containing one or more impurities, including nitrogen dioxide, is purified by passing the gas stream through the bed of metal cation-free silica, alumina or zeolite, thereby removing nitrogen dioxide from the gas stream. The concentration of nitrogen dioxide in the gas stream is generally reduced to not more than about 700 ppm, and is preferably reduced to no more than about 10 ppm, and most preferably reduced to no more than about 3 ppm.

According to a preferred aspect of this embodiment of the invention, the concentration of nitrogen dioxide in the gas stream being treated is reduced to a concentration of about 5000 ppm or less by washing the gas stream with dilute nitric acid and/or water and the washed gas stream is passed through a bed of one or more of the above-mentioned adsorbents to remove nitrogen dioxide. The concentration of nitrogen dioxide exiting the bed of adsorbent is generally reduced to not more than about 700 ppm, and is preferably reduced to no more than about 10 ppm, and is most preferably reduced to no more than about 3 ppm.

In another embodiment, the nitric oxide gas stream is diluted with a sufficient amount of an inert gas, such as nitrogen or argon, to reduce the concentration of nitric oxide in the gas stream to a predetermined concentration, generally to about 5 to about 5000 ppm, and the diluted gas mixture is further purified by passing it through the bed of metal cation-free silica, alumina or zeolite, thereby reducing the concentration of nitrogen dioxide in the diluted gas stream to the desired level.

In a third embodiment, the nitric oxide gas stream is first partially purified by passing it through the bed of metal cation-free silica, alumina or zeolite, thereby reducing the concentration of nitrogen dioxide in the gas stream to a given level, and the partially purified gas stream is diluted with a sufficient amount of an inert gas, such as nitrogen, argon or helium, to reduce the concentration of nitric oxide in the gas stream to the desired final concentration, generally to about 5 to about 5000 ppm.

The conditions under which the adsorption is carried out are not critical. It can be carried out at temperatures in the range of about −50° to about 300° C. or higher, and at absolute pressures in the range of about 0.5 to about 200 bar or higher. To simplify the process, the adsorption is preferably carried out at temperatures in the range of about 0 to about 100° C. and at absolute pressures in the range of 1 to about 10 bar.

The adsorption can be carried out in a single bed of adsorbent or in a battery of two or more adsorption beds arranged in parallel and operated out of phase, so that at least one bed is undergoing adsorption while the adsorbent in another bed is being replaced or regenerated.

DETAILED DESCRIPTION OF THE INVENTION

The nitric oxide that is purified by the process of the invention can be produced by any of several well known manufacturing methods. According to one method, sulfur dioxide and nitric acid are reacted in the presence of water to produce the nitric oxide. A number of byproducts, including sulfuric acid, nitrous oxide (laughing gas) and nitrogen dioxide are produced in this process. The raw product stream also contains unreacted sulfur dioxide. The sulfuric acid is easily removed from the product gas by phase separation followed by water wash. The nitrous oxide does not interfere with the use of the nitric oxide in an inhalation gas since it has a very low toxicity. However, as explained above, nitrogen dioxide, and sulfur dioxide, must be substantially completely removed from the product gas because of the extreme toxicity of these compounds.

Nitric oxide can also be produced by combusting ammonia with oxygen at temperatures of about 1000° C. Byproducts of this process include nitric acid, nitrous acid, nitrous oxide, nitrogen dioxide and nitrogen. The nitric and nitrous acids can be removed by water washing the product gas. Significant quantities of nitrogen dioxide can be removed from the product gas by water washing it with the dilute nitric acid obtained as a byproduct, and subsequently washing the product gas with substantially pure water. Since this process uses oxygen (or air) as a reactant, and since nitric oxide reacts with oxygen to produce nitrogen dioxide, care must be taken to ensure that all of the oxygen is consumed in the reaction. This can be accomplished by conducting the combustion in the presence of excess ammonia.

A third method of producing nitric oxide is by subjecting air to a high voltage electric arc. This procedure is convenient for on site production of small quantities of nitric oxide. Side products which must be removed from the nitric oxide produced by this method include nitrogen dioxide and ozone.

The nitric oxide-rich gas product made by the above processes may contain nitrogen, depending upon which process is used. This poses no problem with respect to the use of the nitric oxide product in inhalation therapy, because nitrogen is nontoxic and is generally used as a diluent for the nitric oxide. The nitric oxide gas is, however, stored in a substantially oxygen-free environment. In this context "substantially oxygen-free" means that the nitric oxide product contains no more than about 10 ppm oxygen. It is important to prevent oxygen from coming into contact with the nitric oxide gas product, since oxygen reacts with nitric oxide to form nitrogen dioxide.

Moisture is also desirably removed from the gas stream prior to or during the adsorption step to avoid corrosion problems during storage. The moisture can be removed by any one or more of various techniques, such as condensation or adsorption. It is preferable to remove sufficient moisture from the gas mixture to render the stream substantially anhydrous. By "substantially anhydrous" is meant the gas stream contains no more than about 500 ppm water vapor. The moisture content can easily be reduced to about 100 ppm or less as it passes through the adsorbent used to remove nitrogen dioxide from the product gas stream.

As mentioned above, the adsorbents used in the invention are adsorbents which are substantially free of metallic cations. Metal cation-free adsorbents which are useful in the invention include silica gel, alumina, and metal cation-free synthetic zeolites, such as types A, X and Y zeolites, and natural zeolites, such as mordenite, faujasite, chabazite, etc. Preferred adsorbents include silica, alumina and types A, X and Y zeolites. The most preferred adsorbent is silica gel. The terms "metal cation-free" and "substantially free of metal cations" when used in reference to an adsorbent, mean that the adsorbent contains no more than trace amounts of metal cations. This feature of the adsorbents used in the invention is important because, as noted above, metal cations catalyze the disproportionation of nitric oxide to nitrogen dioxide and nitrogen.

Metal cation-free zeolites can be prepared, for example, by exchanging the sodium form of a zeolite, such as zeolite type 4A or zeolite type 13X, or the potassium form of the zeolite, with ammonium radicals and subsequently heating the ammonium-exchanged zeolite sufficiently to drive off ammonia, thereby leaving the hydrogen ion, i.e. the proton, as the exchanged cation. The manufacture of proton-exchanged zeolites is well known and forms no part of the present invention.

The conditions under which the adsorption process is carried out are not critical. The adsorption can be carried out at any temperature below the decomposition temperature of the nitric oxide product and the adsorbent, and is generally carried out at the temperature which provides optimum separation. It is preferred to conduct the adsorption process at a temperature which is congruous with other steps of the product manufacturing process, and particularly at atmospheric temperatures and pressures, if possible. Those skilled in the art can easily determine which operating conditions are best suited for their purposes.

When the nitric oxide product gas is to be used in an inhalation gas it is diluted with an oxygen-free inert gas which is nontoxic to humans and animals and which can later be easily blended with oxygen or oxygen-enriched air to make up an inhalation gas having the desired concentration of nitric oxide. Suitable diluent gases include nitrogen, argon, helium, etc. The preferred diluent gas is nitrogen because of the ready availability and low cost of this gas. The nitric oxide-rich gas is preferably diluted with the oxygen-free inert gas to a concentration that can be conveniently blended with the oxygen or oxygen-enriched gas that is used to make up the inhalation gas. Typical inert gas-nitric oxide gas mixtures contain about 5 to about 5000 ppm nitric oxide. Preferred mixtures contain about 5 to about 2000 ppm nitric oxide. The inert gas-nitric oxide mixture can later be blended with oxygen or oxygen-enriched air to provide a gas mixture having the desired nitric oxide concentration (usually in the range of about 0.5 to about 200 ppm nitric oxide).

The process of the invention can be used to directly purify a nitric oxide-rich gas, such as the product obtained from any of the above manufacturing processes, or it can be used to purify an inert gas-nitric oxide concentrate prepared by diluting the nitric oxide-rich gas with an inert gas. In either case the process is effective to reduce the concentration of nitrogen dioxide in the purified gas to any desired value, such as below about 1 ppm. It is generally advantageous to purify the nitric oxide-rich gas prior to dilution, because the volume of gas passed through the adsorbent bed will be relatively small, and also because the concentration of nitrogen dioxide in the inert gas-diluted product can be easily adjusted to any desired final value during the inert gas dilution step.

The adsorbent used in the process of the invention has the additional advantage of effecting the removal of other undesirable impurities, such as water vapor and sulfur dioxide, from the gas stream being purified. This is desirable since, as noted above, water introduces the possibility of corrosion problems, and sulfur dioxide is highly toxic.

Since the quantity of adsorbent necessary to accomplish the desired result will depend not only upon the quantity of gas being treated and the concentration of nitrogen dioxide present in the feed stream, but also on the concentration of other impurities present in the gas stream that are adsorbed by the adsorbent, the size of the adsorbent bed used in the process will be influenced by the amount of impurities present in the gas stream. Thus, a somewhat larger bed of adsorbent may be required if the gas stream being purified contains moisture or other impurities.

The nitrogen dioxide-containing adsorbent can be somewhat regenerated. However, it is difficult to efficiently desorb nitrogen dioxide from the adsorbent; consequently the adsorbent is preferably removed from the adsorbent bed and discarded when it is saturated with nitrogen dioxide. However, moisture can be readily desorbed from the adsorbent used in the invention. Thus, the useful life of the adsorbent can be somewhat extended by regenerating the adsorbent to remove moisture.

The invention is further illustrated by the following examples in which, unless otherwise indicated, parts, percentages and ratios are on a volume basis.

EXAMPLE

A stainless steel cylinder, 13 inches long and having an internal volume of 500 ml was used in this example. The stainless steel cylinder was packed with silica gel, sold by the Davison Chemical Division of W. R. Grace Company as grade No. 41, and a one-half inch layer of cotton wool was inserted into both ends of the tube to hold the adsorbent in place, and to serve as a filter. The test gas was passed through the U-tube at a flow rate of 680 cc/minute. The effluent from the adsorbent bed was collected in a gas holder having an optical path length of 10 meters and a volume of about 2 liters. The gas holder was mounted on a MIDAC G 1002 Fourier Transform Infrared (FTIR) spectrometer which recorded the FTIR measurements at a resolution of 1 cm$^{-1}$. To obtain a high signal/noise ratio 60 scans were used. The gas passed through the cylinder at ambient room temperature and was collected in the gas holder at an absolute pressure of 762 to 766 torr. The feed gas contains 98$^+$% NO and about 4000 ppm $NO_2$. After 60 standard liters of gas was passed through the silica gel bed, $NO_2$ was determined to be less than 1 ppm. The $NO_2$ level increased to about 2 ppm and 5 ppm when the volume of feed gas passed through the bed reached 360 and 530 liters, respectively.

Although the invention has been described with particular reference to specific examples, the examples are merely representative of the invention and variations are contemplated. For instance, mixtures of two or more adsorbents can be used in a single bed or two or more adsorbents can be used in tandem in the process of the invention. The scope of the invention is limited only by the breadth of the appended claims.

What is claimed is:

1. A process for purifying an oxygen-free nitric oxide gas stream containing nitrogen dioxide comprising passing said gas stream through a bed of metal cation-free adsorbent selected from silica, alumina, zeolites and mixtures of these, thereby depleting said gas stream of nitrogen dioxide.

2. The process of claim 1, wherein said metal cation-free adsorbent is selected from silica, alumina, zeolite A, zeolite X, zeolite Y and mixtures of these.

3. The process of claim 1, wherein said gas stream is substantially moisture-free.

4. The process of claim 1, wherein the nitrogen dioxide-depleted gas stream contains not more than about 10 ppm nitrogen dioxide.

5. The process of claim 1, wherein said adsorbent is silica.

6. The process of claim 1, further comprising diluting the nitrogen dioxide-depleted gas stream with inert gas selected from nitrogen, argon, helium and mixtures of these.

7. The process of claim 6, wherein said nitrogen dioxide-depleted gas is diluted with sufficient inert gas to reduce the concentration of nitrogen dioxide in said nitrogen dioxide-depleted gas to not more than about 1 ppm.

8. The process of claim 6, further comprising humidifying the nitrogen dioxide-depleted gas stream.

9. The process of claim 6, further comprising blending the inert gas-diluted gas stream with a gas selected from oxygen or oxygen-enriched air to produce a blended mixture containing about 0.5 to about 200 ppm nitric oxide.

10. The process of claim 1, further comprising removing nitrogen dioxide from said gas stream prior to passing it through said bed of adsorbent by scrubbing the gas stream with an aqueous liquid, or by subjecting the gas stream to cryogenic distillation or by a combination of these procedures.

11. The process of claim 1, further comprising blending the purified gas stream with a gas selected from oxygen or oxygen-enriched air to produce a blended mixture containing about 0.5 to about 200 ppm nitric oxide.

12. The process of claim 11, further comprising humidifying said blended mixture.

13. The process of claim 1, wherein said gas stream contains water vapor and the concentration of water vapor in said gas stream is reduced to not more than about 100 ppm as said gas stream passes through said adsorbent.

14. The process of claim 1, wherein said gas stream contains one or more impurities selected from sulfur dioxide and ozone and the concentration of each of said one or more impurities in said gas stream is reduced to not more than about 1 ppm as said gas stream passes through said adsorbent.

15. A method of removing nitrogen dioxide from a gas stream containing nitric oxide and at least about 10 ppm nitrogen dioxide comprising passing said gas stream through a bed of metal cation-free adsorbent selected from silica, alumina, zeolite A, zeolite X, zeolite Y and mixtures of these, thereby producing a nitrogen dioxide-depleted gas containing not more than about 5 ppm nitrogen dioxide.

16. The process of claim 15, wherein said gas stream additionally comprises nitrogen.

17. A process for preparing an inert gas-nitric oxide gaseous product containing about 5 to about 5000 ppm nitric oxide comprising passing a gas stream containing nitric oxide and nitrogen dioxide through a bed of metal cation-free adsorbent selected from silica, alumina, zeolite A, zeolite X, zeolite Y and mixtures of these, thereby producing a nitrogen dioxide-depleted gas, and diluting the nitrogen dioxide-depleted gas with an inert gas.

18. The process of claim 17, wherein said nitrogen dioxide-depleted gas is diluted with sufficient inert gas to reduce the concentration of nitrogen dioxide therein to not more than about 10 ppm.

19. The process of claim 17, wherein said adsorbent is silica.

20. The process of claim 17, wherein said inert gas is nitrogen.

21. A process for preparing an inert gas-nitric oxide gaseous product comprising blending a gas stream containing nitric oxide and nitrogen dioxide with sufficient inert gas to reduce the concentration of nitric oxide in the gas stream to about 5 to about 5000 ppm, and passing said gas stream through a bed of metal cation-free adsorbent selected from silica, alumina, zeolite A, zeolite X, zeolite Y or mixtures of these, thereby producing a nitrogen dioxide-depleted gas stream.

22. The process of claim 21, further comprising diluting said nitrogen dioxide-depleted gas stream with sufficient inert gas to reduce the nitrogen dioxide therein to not more than about 10 ppm nitrogen dioxide.

23. The process of claim 21, wherein said adsorbent is silica.

24. The process of claim 21, wherein said inert gas is selected from nitrogen, argon and mixtures of these.

25. The process of claim 24, wherein said inert gas is nitrogen.

* * * * *